United States Patent
Singer (10) Patent No.: US 9,334,501 B2
(45) Date of Patent: May 10, 2016

(54) SIRNA AGAINST P22PHOX (76) Inventor: Donald R. Singer, Leamington Spa (GB)

(*) Notice: Subject to any disclaimer, the term of this patent is extended or adjusted under 35 U.S.C. 154(b) by 29 days.

(21) Appl. No.: 13/825,830

(22) PCT Filed: Sep. 23, 2011

(86) PCT No.: PCT/GB2011/051802
§ 371 (c)(1),
(2), (4) Date: Jun. 21, 2013

(87) PCT Pub. No.: WO2012/038759
PCT Pub. Date: Mar. 29, 2012

(65) Prior Publication Data
US 2013/0274312 A1 Oct. 17, 2013

(30) Foreign Application Priority Data

Sep. 23, 2010 (GB) .................................. 1015974.7

(51) Int. Cl.
*C12N 15/11* (2006.01)
*C12N 15/113* (2010.01)
*F16D 55/40* (2006.01)
*F16D 65/853* (2006.01)
*F16D 65/12* (2006.01)
*F16D 55/00* (2006.01)

(52) U.S. Cl.
CPC ............ *C12N 15/1137* (2013.01); *F16D 55/40* (2013.01); *F16D 65/853* (2013.01); *C12N 2310/14* (2013.01); *C12N 2320/10* (2013.01); *F16D 65/126* (2013.01); *F16D 2055/0058* (2013.01); *F16D 2055/0095* (2013.01)

(58) Field of Classification Search
CPC .......................... C12N 15/113; C12N 2310/14
See application file for complete search history.

(56) References Cited

U.S. PATENT DOCUMENTS

| 2008/0039420 | A1* | 2/2008 | Juhasz et al. ..................... 514/44 |
| 2011/0112168 | A1* | 5/2011 | Feinstein et al. ............. 514/44 A |
| 2011/0190380 | A1* | 8/2011 | Feinstein et al. ............. 514/44 A |
| 2012/0108654 | A1* | 5/2012 | Campochiaro ............. 514/44 R |

FOREIGN PATENT DOCUMENTS

| WO | WO 2005/103297 A1 * 11/2005 |
| WO | WO 2009/044392 A2 * 4/2009 |

OTHER PUBLICATIONS

Li et al. Mol. Ther. 2008 16:1688-94.*
Suzuki et al. IJBCB 35 (2003) 881-900.*

* cited by examiner

Primary Examiner — Brian Whiteman
(74) Attorney, Agent, or Firm — Cantor Colburn LLP (57) ABSTRACT

The invention relates to siRNA against p22phox, compositions comprising the siRNA, methods of treating diseases with the siRNA and cell based systems for studying the effect of p22 phox modulation by siRNA or cells.

13 Claims, 6 Drawing Sheets

A

```
ORIGIN Genebank access no=M21186
    1 gcagtgtccc agccgggttc gtgtcgccat ggggcagatc gagtgggcca tgtgggccaa
   61 cgagcaggcg ctggcgtccg gcctgatcct catcaccggg ggcatcgtgg ccacagctgg
  121 gcgcttcacc cagtggtact ttggtgccta ctccattgtg gcgggcgtgt tgtgtgcct
  181 gctggagtac ccccggggga agaggaagaa gggctccacc atggagcgct ggggacagaa
  241 gcacatgacc gccgtggtga agctgttcgg gccctttacc aggaattact atgttcgggc
  301 cgtcctgcat ctcctgctct cggtgcccgc cggcttcctg ctggccacca tccttgggac
  361 cgcctgcctg gccattgcga gcggcatcta cctactgggg gctgtgcgtg gcgagcagtg
  421 gacgcccatc gagcccaagc cccgggagcg gccgcagatc ggaggcacca tcaagcagcc
  481 gcccagcaac ccccgccgc ggcccccggc cgaggcccgc aagaagccca gcgaggagga
  541 ggctgcggcg gcggcgggg gaccccgggg aggtccccag gtcaaccccca tcccggtgac
  601 cgacgaggtc gtgtgacctc gccccggacc tgccctccca ccaggtgcac ccacctgcaa
  661 taaacgcagc gaaggccggg aaaaaaa (SEQ ID NO: 1)
```

B

```
Query   43  CCATGGGGCAGATCGAGTGGGCCATGTGGGCCAACGAACAGGCGCTGGCATCTGGCCTGA  102
            ||||||||||||||||||||||||||||||||||||||| |||||||||| || |||||
Sbjct   27  CCATGGGGCAGATCGAGTGGGCCATGTGGGCCAACGAGCAGGCGCTGGCGTCCGGCCTGA   86

Query  103  TCCTCATCACAGGGGGCATCGTGGCTACTGCGGGACGCTTCACGCAGTGGTACTTTGGTG  162
            |||||||||| |||||||||||||||| || || || |||||||| ||||||||||||||
Sbjct   87  TCCTCATCACCGGGGGCATCGTGGCCACAGCTGGGCGCTTCACCCAGTGGTACTTTGGTG  146

Query  163  CTTACTCTATTGTTGCAGGAGTGCTCATCTGTCTGCTGGAGTACCCCGGGGAAAGAGGA  222
            | |||| ||||| || ||| |   | || |||||||||||||||||||  ||||||||
Sbjct  147  CCTACTCCATTGTGGCGGGCGTGTTTGTGTGCCTGCTGGAGTACCCCGGGGGAAGAGGA  206

Query  223  AAAAGGGCTCCACCATGGAGCGGTGTGGACAGAAGTACCTGACCGCTGTGGTGAAGCTGT  282
             |||||||||||||||||||||| ||| ||||||||| || ||||||| |||||||||||
Sbjct  207  AGAAGGGCTCCACCATGGAGCGCTGGGGACAGAAGCACATGACCGCCGTGGTGAAGCTGT  266

Query  283  TCGGGCCCCTCACCAGAAATTACTACGTCCGGGCTGTCCTCCACTTACTGCTGTCCGTGC  342
            ||||||||  | |||||  |||||||| ||||| ||||| ||  | ||||| || ||||
Sbjct  267  TCGGGCCCTTTACCAGGAATTACTATGTTCGGGCCGTCCTGCATCTCCTGCTCTCGGTGC  326

Query  343  CTGCAGGCTTCCTGCTGGCCACCATCCTGGGGACCGTCTGCTTGGCCATTGCCAGTGTGA  402
            | || ||||||||||||||||||||||| || |||| ||||  ||||||||||   |  |
Sbjct  327  CCGCCGGCTTCCTGCTGGCCACCATCCTTGGGACCGCCTGCCTGGCCATTGCGAGCGGCA  386

Query  403  TCTACCTGCTGGCAGCCATCCGGGGTGAGCAGTGGACTCCCATTGAGCCTAAACCCAAGG  462
            ||||||| |||||  | || ||||||| |||||||| || |||||||||||| ||| ||
Sbjct  387  TCTACCTACTGGCGGCTGTGCGTGGCGAGCAGTGGACGCCCATCGAGCCCAAGCCCCGGG  446

Query  463  AGCGGCCGCAGGTTGGAGGCACCATCAAGCAGCCACCTACCAACCCCCCACCCCGGCCAC  522
            |||||||||| | |||||||||||||||||||| |  ||||||||||| || |||||
Sbjct  447  AGCGGCCGCAGATCGGAGGCACCATCAAGCAGCCGCCCAGCAACCCCCGCCGCGGCCCC  506

Query  523  CAGCGGAGGTCCGCAAGAAGCCAAGTGAGG  552 (SEQ ID NO: 11)
            | || |||| ||||||||||||| || ||||
Sbjct  507  CGGCCGAGGCCCGCAAGAAGCCCAGCGAGG  536 (SEQ ID NO: 12)
```

SIRNA AGAINST P22PHOX

CROSS-REFERENCE TO RELATED APPLICATIONS

This application is a U.S. National Stage application of International Application Ser. No. PCT/GB2011/051802 filed Sep. 23, 2011, and claiming priority to GB 1015974.7 filed Sep. 23, 2010. All of these applications are incorporated by reference in their entireties.

The invention provides siRNA against p22phox, compositions comprising the siRNA, methods of treating diseases with the siRNA, and cell based systems for studying the effect of p22phox modulation by the siRNA on cells.

Angiogenesis, the formation of new blood vessels, is critical to many important physiological processes. Abnormal angiogenesis plays a key role in a wide range of serious cardiovascular disorders including hypertension, atherosclerosis and ischemic heart disease[1-3]. Data from in vivo and in vitro studies in a wide range of non-human and human tissues including myocardium[4], skeletal muscle[5], conjunctiva, buccal membranes and retinal circulation[6], suggest impaired angiogenesis as an important feature in hypertension[6,7]. The inventors and others have shown that microvascular rarefaction is a common feature in subjects with borderline hypertension[8] in patients with established essential hypertension[8] and in pregnant women with pre-eclamptic toxaemia[10]. These findings suggest that capillary rarefaction is likely to occur as a primary or a very early structural abnormality in essential hypertension (see review[11]).

Reactive oxygen species (ROS), such as superoxide anion and hydrogen peroxide ($H_2O_2$), are involved in signalling pathways in many aspects of growth factor-mediated angiogenesis[3]. High concentrations of ROS cause oxidative stress and apoptosis, important features of common disorders associated with cardiovascular disease, including hypertension, atherosclerosis, diabetes mellitus and renal impairment[3,12]. In contrast, ROS at low concentrations are involved in endothelial cell (EC) proliferation and migration, and are key to angiogenesis in vivo[3, 13-16]. The major source of ROS in ECs is generation via the NAD(P)H oxidase complex[17]. NADPH oxidase subunits (Nox1, Nox2 (gp91phox), Nox4, p22phox, p47phox, p67phox and the small G protein Rac1) are expressed in ECs[3, 18, 19]. However, the levels of expression of different NAD(P)H oxidase subunits vary between different cell types including vascular smooth muscle cells (VSMC), neutrophils and ECs[20]. The p22phox subunit is an essential component of the NAD(P)H oxidase enzymatic complex[21]. In VSMC, Nox2 and p22phox form the electron transfer component of the oxidase; p47phox and p67phox are cytosolic components interacting with Nox 2 and p22phox to modulate enzyme activity[20]. Increasing evidence suggests that p22phox may play a key role in hypertension[22]. For example, angiotensin II (Ang II), a potent stimulator for NADPH oxidase[12, 17], activates p22phox in VSMCs in hypertensive rats during infusion with Ang II[23], with a parallel increase of p22phox mRNA in the aorta in these rats[24]. Ang II increases arterial blood pressure and renal p22phox mRNA and protein levels[25], whereas knocking down p22phox with small interference RNA (siRNA) reduces Ang-II-induced hypertension in rats[25]. The authors of that paper[25] reported RNA silencing in vivo of p22phox in rats. Double-stranded interfering RNAs (siRNAs) targetted to p22phox tested its role in mediating responses to Ang-II and hypertension in rats. Two siRNAs were observed to reduce mRNA in cultured smooth muscle cells. The siRNAs were observed to decrease protein expression for Nox-1, -2 and -4 in Ang-11 infused rats[25]. It was reported that p22phox is required for renal NADPH oxidase activity, expression of Nox proteins and contributes to hypertension during Mg-II slow-repressor response. Two different siRNAs are indicated as having been used. The online supplement for the paper indicates that the two sequences were directed towards 299-320 and 574-595 of the rat p22phox sequence. These correspond to 284-304 (with a 3 nucleotide mismatch) and 574-595 of the human p22phox sequences. As discussed below, the first sequence was not found to be effective by the inventors using siRNA against the human p22phox sequence.

In human studies, the 930G allele of p22phox polymorphism is associated with higher promoter activity, increased NADPH oxidase-mediated oxidative stress and hypertension[26]. Furthermore, the C242T polymorphism of p22phox is associated with vascular ageing in elderly Korean subjects[27], and is also associated with progression of asymptomatic atherosclerosis in Japanese subjects with type 2 diabetes, and with insulin resistance in non-diabetic subjects[28, 29], or coronary heart disease in the Chinese population[30].

Although p22phox is abundantly expressed in VSMCs, its expression in ECs is much lower[20]. However, the p22phox subunit may also play an essential role in NAD(P)H oxidase enzymatic complex in ECs[21]. For example, p22phox is required for Ang II and thrombin-stimulated ROS formation in ECs[31,32]. AngII stimulated NADPH oxidase activity in ECs is regulated by serine phosphorylation of p47phox and enhanced binding of p47phox to p22phox[33]. ROS generated by NADPH oxidase activation stimulates diverse redox signalling pathways, such as mitogen-activated protein kinases, Akt and endothelial nitric oxide synthase (eNOS), which are essential for EC migration and proliferation[34].

The discovery of RNA interference (RNAi) has offered great potential for therapeutic application using siRNA in the treatment of diseases (RNAi therapy), and deeper understanding of regulation of gene function through knocking down expression of specific genes by siRNAs. RNAi therapy offers a powerful option to treat diseases difficult to treat with existing drugs[35]. For example, phase I studies to investigate RNAi-based drugs for age-related macular degeneration (a leading cause of blindness) and respiratory syncytical virus, (the leading cause of paediatric hospitalisations) have already been completed[35]. RNAi therapy for the treatment of HIV is about to enter clinical trials[36]. Given the critical role of NADPH oxidase in the modulation of vascular function, NADPH oxidase has been proposed to be a therapeutic target in vascular disease[37]. To develop RNAi therapy targeted at NADPH oxidase, the inventors aimed to target against p22phox, as p22phox might be a critical subunit regulating NADPH oxidase in human ECs. For initial testing of proof of concept, they used the human umbilical vein endothelial cell system, which is a well-established model for the study of EC survival and angiogenesis[38]. Thus, the aims of the inventors were: 1) to determine siRNA targeting p22phox (sip22phox) sequences that might effectively knock down p22phox expression; and 2) to determine whether angiogenesis and key parameters relevant to angiogenesis in human umbilical vein endothelial cells were affected by knocking down p22phox with sip22phox.

A first aspect of the invention provides an siRNA comprising a sense region and an anti-sense region, wherein said sense region and said anti-sense region form a duplex region, said sense region and said anti-sense region are each 18-30 nucleotides in length and said anti-sense region comprises a nucleotide sequence that is at least 80% complementary to a contiguous sequence of at least 18 nucleotides from position 209 to 279 of the nucleotide sequence of p22phox.

The nucleotide sequence is preferably that of human p22phos, and is preferably as shown in FIG. 1a (SEQ ID NO:1).

However, the sequence may be from any mammalian nucleotide sequence encoding p22phox, depending, for example, on whether the siRNA is to be used in human cells or another mammal's cells. FIG. 1b shows the alignment of rat and human p22phox (SEQ ID NOS: 11 and 12). Positions 239-259 of the human sequence have 85.6% homology with the rat sequence. The sequence either side extending to 209 on one side has 93.3% homology and extending to 279 on the other 90.4% homology.

Small interfering RNA (siRNA) are double-stranded RNA molecules that interfere with the expression of a specific gene. In the case of the current invention they restrict expression of the p22phox gene. Preferably the maximum amount of reduction in the expression of the p22phox gene, as determined by mRNA levels, is at least 40%, most preferably at least 50%, at least 60% or at least 70%, in comparison to the absence of the siRNA molecule.

Preferably the length of the duplex region is 19-28 nucleotides in length, more preferably 20-25 nucleotides in length, most preferably 21 nucleotides in length.

The anti-sense region is preferably at least 85, at least 90, at least 92, at least 93, at least 94, at least 95, at least 96, at least 97, at least 98, at least 99, preferably 100% complementary to the contiguous sequence.

Preferably the anti-sense region comprises a nucleotide sequence which is complementary to a contiguous sequence of at least 18 nucleotides of at least a portion of the nucleotide sequence from positions 239-259.

Preferably the nucleotide sequence is complementary to a contiguous sequence of at least 18 nucleotides of the nucleotide sequence from 239-259.

Preferably the anti-sense region is not complementary to a region of the sequence which overlaps with positions 284-304 of the p22phox sequence shown in FIG. 1a.

siRNA may be in the form of two separate strands of RNA which are complementary to each other and hybridised together to form a double stranded region of RNA. However, it may also be formed from a single strand of RNA, in the form of a so-called hairpin loop with the complementary regions hybridised together. Such hairpin loops typically comprise a linking region between the duplex region of 4-11 nucleotides.

The siRNA may comprise a short overhang at one end or the other, or indeed both ends of the duplex region. Typically this may be one or two nucleotides. The overhang may comprise one or more deoxythymidine nucleotides.

Preferably the sense and anti-sense sequences used to form the siRNA are:

```
                                              (SEQ ID NO: 2)
    5'-AAG CAC ATG ACC GCC GTG GTG-3'
    (sense, 239-259),
    and (SEQ ID NO: 3)
    5'-AAC ACC ACG GCG GTC ATG TGC-3'
    (antisense).
```

In an alternative embodiment to the invention, the siRNA comprising a sense region and an anti-sense region, may comprise an anti-sense region that is at least 90% complementary to a contiguous sequence of at least 18 nucleotides from position 584-604 of the p22 phox sequence shown in FIG. 1a.

The level of complementarity, preferred lengths of the regions and construction of the siRNA may be as defined for the siRNAs of the first aspect of the invention.

Preferably the siRNA sequences are:

```
                                              (SEQ ID NO: 4)
    5'-AAC CCC ATC CCG GTG ACC GAC-3'
    (sense, 584-604)
    and (SEQ ID NO: 5)
    5'-AAG TCG GTC ACC GGG ATG GGG-3'
    (antisense)
```

The siRNAs, according to any aspect of the invention, may be made by methods generally known in the art.

The siRNAs of the invention may utilise one or more uracil residues instead of thymidine residues. The siRNA may also comprise one or more modified nucleotides, such as 2'-O-methyl nucleotide or a 2'-O-(2-methoxyethyl) nucleotide.

The siRNAs, according to the invention, may be provided in a composition comprising the siRNA in combination with a suitable delivery agent for introducing the siRNA into a cell either in vitro or indeed in vivo. Methods of introducing siRNAs into cells are generally known in the art. For example, Modlinger (Ref. 25) utilises a commercially available polymer sold under the trademark "TransIT", which is available from Mirus Inc.

Alternatively, an active siRNA may be produced from a plasmid or viral vector expressing, for example, a short hairpin RNA (shRNA) that is subsequently processed into the active siRNA. Such vectors, including adenoviral vectors, are generally known in the art.

Methods of modulating angiogenesis and/or oxidative-stress using the siRNA or compositions of the invention are also provided.

Preferably the method is used to suppress tumour angiogenesis, for atheromatous plaque stabilisation or to reduce abnormal blood vessel formation in diabetes mellitus in retinal, renal and other circulations, or retinosis.

The invention also provides a method of modulating infective and/or inflammatory disorders, neoplastic disease and/or systemic and neuro-degenerative diseases comprising administering an effective amount of a siRNA or a composition according to the invention.

A further aspect of the invention provides a method of treating tumours comprising administering an effective amount of a siRNA or a composition according to the invention.

A further aspect of the invention provides an isolated nucleotide sequence encoding at least one of the sense region and/or anti-sense region of a siRNA according to the invention, but no more than 30 contiguous nucleotides of the sequence shown in FIG. 1a or 1b or a sequence complementary to the nucleotide sequence thereof. The nucleotide sequence may encode a short hairpin RNA. The nucleotide sequence may be a part of a plasmid or adenoviral vector to allow the siRNA to be produced either in vivo or alternatively in vitro.

siRNA molecules, according to the invention, may be delivered intravenously, intradermally, intramuscularly, intrathecally, intranasally, orally or intraperitoneally.

The siRNAs of the invention may be used to study the effect of modulating p22phox on cells. Such a use may be used to identify, for example, the pathways in which p22phox is involved, be used to model, for example, angiogenesis, and may be used to identify new compounds capable of interacting with the angiogenesis pathways, or other pathways, with which p22phox is involved.

Accordingly, a further aspect of the invention provides a method of studying an effect of p22phox modulation on a cell comprising contacting the cell with a siRNA or composition according to any aspect of the invention and detecting one or more physiological and/or chemical changes in the cell.

The cell may be, for example, grown in vitro such as in tissue culture. Alternatively, the cell may be within an organism, such as a rodent (e.g. rat) animal model.

Preferably the cell is a tissue culture cell, or other cell grown in vitro. Preferred cells include endothelial cells from human or animals. Preferably the cell is a human endothelial cell, such as a human umbilical vein endothelial cell or a tissue culture cell such as HUV-EC-C.

The inventors have identified that preferred concentrations are between 5 nmol/L and 10 nmol/L siRNA in growth media.

The method may be used to identify an effect of p22phox or another compound on angiogenesis.

The inventors have newly identified the role of p22phox in angiogenesis. Accordingly a still further aspect of the invention provides a method of studying angiogenesis comprising contacting an endothelial cell with an siRNA specific for p22phox and capable of inhibiting mRNA levels of p22phox in a cell as defined above. This may be an siRNA according to the invention or alternatively another siRNA capable of inhibiting the production of p22phox mRNA.

As discussed in the Materials and Methods, it has been observed that the presence of angiotensin II has an effect on the pathways in which p22phox is involved. Accordingly the methods of the invention may additionally comprise a step of contacting a cell with angiotensin II.

The physiological and/or chemical changes to the cell include, for example, the degree of cell adhesion, proliferation, migration and/or vascular tube formation. For example, adhesion may be measured by observing VE-caherin levels. As discussed in the Materials and Methods section, cell migration assays may be undertaken using an invasion chamber.

Vascular tube formation may be observed using a Matrigel layer as discussed below. The inventors also observed that the siRNA in cells had an effect on Akt phosphorylation. This is a key molecule involved in endothelial cell migration and proliferation. Moreover, apoptosis may be observed. The inventors have found that by studying the effect on caspase 3-cleavage, p22phox has an effect on apoptosis in cells.

A still further aspect of the invention provides a cell comprising an siRNA according to the invention. The cell may be in vitro or in vivo, and may be an isolated cell type or alternatively a part of a whole mammalian organism.

The invention will now be described by way of example only, with reference to the following figures:

FIG. 1a. p22phox human nucleotide sequence (GenBank access No. M21186) showing positions of siRNAs studied.

FIG. 1b. Comparison of rat (*Rattus norvegicus*) and human p22phox sequences.

FIG. 1B. p22phox mRNA levels showed a dose responsive reduction following transfection with siRNA (P2) at 1, 5 and 10 nmol/L. *p<0.001.

CN: control, lipo: lipofectamine, cells treated with lipofectamine only.

FIG. 3. Quantification of p22phox protein levels and ROS generation. 20 µg of protein were loaded on each lane for the analysis of p22phox protein levels with western blotting (FIG. 2A, AU: arbitrary units) in the presence of angiotensin II (1 µM) and siRNA at either 5 or 10 nmol/L approximately 24 hrs post transfection. Levels of β-actin were analysed to control for equal loading. *p<0.05, ***p<0.001 (siRNA treated group vs. control group); $^{xxx}$p<0.001 (siRNA plus Ang II treated group vs. Ang II only treated group).

FIG. 3B. ROS generation analysed using the DHE staining method. Transfected ECs with 10 nmol/L siRNA were cultured in Ham's F-12K medium (10% FCS) to ~80% confluence, and replaced with serum free medium and cultured for overnight. The cells were then treated either with or without Ang II at 1 µM for 4 hrs before DHE 10 µM (diluted by DMSO under nitrogen gas) was added to the medium and incubated for 30 min. Generation of ROS was recorded under a fluorescence microscope (magnification: 20×).

FIG. 4A. Vascular endothelial cadherin (VE-Cadherin) protein expression was analysed using fluorescence labelled antibody. After overnight incubation with the first antibody at 4° C., cells were washed with PBS and added with the second antibody (goat—anti-rabbit FITC) at 1:200 dilution and incubated at 37° C. for 1 hr. The cells were washed with PBS (×3) and mounted with DAPI. The positive staining was calculated by Image J software. Magnification: 40×.

FIG. 4B. Cell proliferation rate analysed using the MTT assay. Cells were seeded onto gelatine-coated 96-well plates at a density of ~1-3×10$^4$ cells per well. After an overnight culture the cells were transfected with siRNAs (either 5 or 10 nmol/L) and added with either Ang II (1 µM) ~4 hrs post transfection. MTT (2 mg/ml in PBS) was added to each well and incubated for a further 4 hrs. The media containing MTT was removed, and formazan crystals were dissolved in 200 µl of DMSO per well. The absorbance was read at 570 nm FIG. 4C. Cell migration assay undertaken using an invasion chamber (BD Bioscience). Endothelial cells were seeded (in triplicates) on the upper chambers at ~10$^4$ cells/well on 24-well plates pre-coated with 0.1% matrigel on the lower chamber. After overnight incubation at 37° 5% CO$_2$, non-invading cells were removed from the upper surface of the membrane by scrubbing. The migrated cells attached to the bottom surface were stained with hematoxylin-eosin (H-E).

FIG. 5. Vascular tube formation in endothelial cells treated with siRNA or angiotensin II. Thawed Matrigel (200 µl) was added to 24-well plates and then incubated at 37° C. for 30 minutes to form a gel layer. Transfected cells (~10$^4$ cells/well) were seeded to the Matrigel-coated 24-well plates, treated with/without Ang II (1 µM) before transfection and incubated in Ham's F-12K medium containing 10% FBS for 4 hr. Tube formation at 4 hrs or 18 hrs was recorded with phase contrast microscopy. Images were captured using a Scion digital camera (magnification: 10×) and analyzed using Imaging J software. *p<0.05, ***p<0.001 (treated group vs. control group).

FIG. 6. Analysis of Akt phosphorylation and caspase-3 cleavage pathways in endothelial cells with western blotting. ~20 µg of supernatant was resolved on SDS-PAGE gel. Separated proteins were transferred on to nitrocellulose membrane. The membrane was blocked with 5% low-fat milk for 1 hr at room temperature and incubated with specific antibodies against either phosphorylated Akt or cleaved caspase-3 (1:1000, Cell-Signalling) at 4° C. overnight. An antibody against β-actin (1:100) was used as a control for equal loading of protein. The membrane was washed twice and incubated with a second antibody (1:2000) at room temperature for 1 hr. The immunoreactive protein was detected using enhanced chemiluminescence (ECL) plus (Amersham) and developed with KODAK film in dark room. The blotting film was quantitatively analyzed with Syngene Genetools (Bio Imaging systems) software. ***$p<0.001$ (treated group vs. control group).

METHODS

Synthesis of siRNAs Targeting p22phox (sip22phox) and Transfection of Human Endothelial Cell Line Three target sequences were identified from human p22phox (Genebank a/c No. M21186) mRNA sequence for synthesis of sip22phox, based on the inventors' previous experience in siRNA design[39,40]. A number of potential sequences were considered. However, the best with which to proceed were considered to be: 1) 5'-AAT TAC TAT GTT CGG GCC GTC-3' (sense, 284-304 (SEQ ID NO:6) and 5'-AAG ACG GCC CGA ACA TAG TAA-3' (antisense) (SEQ ID NO:7); 2) 5'-AAG CAC ATG ACC GCC GTG GTG-3' (sense, 239-259) (SEQ ID NO:2) and 5'-AAC ACC ACG GCG GTC ATG TGC-3' (antisense) (SEQ ID NO:3); and 3) 5'-AAC CCC ATC CCG GTG ACC GAC-3' (sense, 584-604) (SEQ ID NO:4) and 5'-AAG TCG GTC ACC GGG ATG GGG-3' (antisense) (SEQ ID NO:5). DNA oligos were synthesized commercially (Thermofisher) and sip22phox were synthesized in vitro using a kit according to the manufacturer's instruction (Ambion).

Human endothelial cells (HUV-EC-C, ATCC-CRL-1730) were cultured in Ham's F-12K medium (ATCC) containing 10% foetal calf serum (FCS), 100 µg/ml heparin (Sigma) and 75 µg/ml human ECGS (Sigma). Cells (~80% confluence) were replaced with growth medium without antibiotics the day before transfection. To establish a transfection protocol, fluorescence labelled siRNAs (BLOCK-iT) were mixed with Lipofectamine 2000 (Invitrogen) in serum-free medium and incubated at room temperature (RT) for 20 min, before being added to cells and incubated in serum-free medium at 37° C. in 5% $CO_2$ for 4-6 hrs. Then, the medium was replaced with growth medium containing 10% FCS and antibiotics overnight. The transfection efficiencies for fluorescence labelled siRNAs were: ~51% at 1 nmol/L, ~87% at 5 nmol/L and ~96% at 10 nmol/L. Thus, siRNAs at 5 nmol/L or 10 nmol/L were used in our studies.

Quantification of p22phox mRNA Levels

Total RNAs were prepared from cells ~24 hrs post-transfection using a SV total RNA isolation kit (Promega). To synthesise cDNA, total RNA (1 µg in 12.5 µl of RNAse free $H_2O$) was denatured at 70° C. for five minutes and chilled to 4° C., added with 0.5 mM dNTP, 5 µM random hexamers, 10 units/µl of MMLV reverse transcriptase (Promega, Southampton, UK), 1.0 units/µl RNAsin (Promega), in 1×MMLV reverse transcriptase buffer containing 50 mM Tris-HCl (pH 8.3 at 25° C.), 75 mM KCl, 3 mM $MgCl_2$, 10 mM DTT and DEPC—$H_2O$ to a final volume of 20 µl. The cDNA reaction was incubated for 1 hr at 42° C. and stopped by heating at 95° C. for 5 minutes.

Primers and probe for real-time PCR were designed and synthesized by ABI. The PCR primers were: 5'-GTCCGGCCTGATCCTCATC-3' (sense) (SEQ ID NO:8) and 5'-GCCCGCCACAATGGAGTA-3' (antisense) (SEQ ID NO:9). The probe sequence was: 5'-CACCCAGTGGTACTTTG-3' (SEQ ID NO:10). The PCR reactions were undertaken in a 96-well plate with a total volume of 25 µl/reaction, containing 12.5 µl TagMan universal PCR Master Mix, 1.25 µl 20×Assay Mix (Primer & probe) and 11.25 µl cDNA (either diluted by 1:5 or 1:10 before added to the reactions). 18S rRNA was amplified as positive control. The PCR reaction conditions were: a pre-run of 50° C. for 2 min and a single denature step at 95° C. for 10 min, followed by 95° C. for 15 sec and annealing at 60° C. for 1 min for up to 40 cycles. SABI 7500 relative quantification system software was applied for data analysis.

Western Blotting

Cells were lysed with 1× modified RIPA buffer with proteases (Upstate, 1% Triton X-100, 158 mM NaCl, 5 mM EDTA, 10 mM Tris-HCl, pH 7.2, 100 mM sodium vanadate, 10 µg/ml leupeptin, 10 µg/ml aprotinin and 1 mM PMSF) on ice ~24 hrs post siRNA transfection. Cell lysates were sonicated for 15 seconds, boiled at 100° C. for 5 min and cooled at room temperature, and was centrifuged at 12000×g for 10 min at 4° C. and cell debris was removed. An aliquot of the cell lysate was used for protein assay using a kit (Bio-Rad). 20 µg of supernatant per sample was resolved on SDS-PAGE gel. Separated proteins were transferred on to nitrocellulose membrane. The membrane was blocked with 5% low-fat milk for 1 hr at room temperature and incubated with specific antibodies against either p22-phox (FL-195, 1:400, Santa-Cruz), phosphorylated Akt or cleaved caspase-3 (1:1000, Cell-Signalling) at 4° C. overnight. An antibody against β-actin (1:100) was used as a control for equal loading of protein. The membrane was washed twice and incubated with a second antibody (1:2000) at room temperature for 1 hr. The immunoreactive protein was detected using enhanced chemiluminescence (ECL) plus (Amersham) and developed with KODAK film in dark room. The blotting film was quantitatively analyzed with Syngene Genetools (Bio Imaging systems) software.

ROS Production Measured Using DHE Staining

The ROS production in ECs was measured using dihydroethidium (DHE, Sigma) which generated rhodamine in response to stimulation of ROS with phorbol 12-myristate 13-acetate. Fluorescence was monitored by excitation at 480 nm and 540 nm wavelengths. ECs transfected with 10 nmol/L siRNA were cultured in Ham's F-12K medium (10% FCS) to ~80% confluence, and replaced with serum free medium and cultured overnight. The cells were then treated either with or without Ang II at 1 µmol/L for 4 hrs before DHE 10 µmol/L (diluted by DMSO under nitrogen gas) was added to the medium and incubated for 30 min. Generation of ROS was recorded under a fluorescence microscope.

Immunofluorescent Staining of Endothelial Cells Adhesive Ability

Anti-human VE-cadherin (vascular endothelium cadherin, also known as cadherin-5) antibody (Santa Cruz) was used to analyze the adhesive ability of ECs. Second antibody was goat—anti-rabbit FITC. After overnight incubation with the first antibody at 4° C., cells were washed with PBS, and the second antibody was added at 1:200 dilution and incubated at 37° C. for 1 hr. The cells were washed with PBS (×3) and mounted with DAPI. The cells were observed under fluorescent microscopy. The positive staining was calculated by Image J software.

MTT (Thiazolyl Blue Tetrazolium Bromide) Assay

The proliferation rate of ECs was estimated by measuring the ability of live cells to metabolise MTT to formazan[41]. Cells were seeded on to a gelatine-coated 96-well plate at a density of ~1-3×$10^4$ cells per well. After overnight culture the cells were transfected with siRNAs and added with either Ang II ~4 hrs post transfection. MTT (2 mg/ml in PBS) was added to each well and incubated for a further 4 hrs. The media containing MTT was removed, formazan crystals were dissolved in 200 µl of DMSO per well, and absorbance was read at OD570 nm.

In Vitro Migration Assay

The migration assay was undertaken using an invasion chamber (BD Bioscience). Endothelial cells were seeded (in triplicates) on the upper chambers at ~$10^4$ cells/well on 24-well plates pre-coated with Matrigel on the lower chamber. After overnight incubation at 37° in 5% $CO_2$, non-invading cells were removed from the upper surface of the membrane by scrubbing. The migrated cells attached to the bottom surface were stained with hematoxylin-eosin (H-E).

Matrigel Coated 3-D Tube Formation Assay

Matrigel was stored at 4° C. Thawed Matrigel (200 µl) was added to 24-well plates and incubated at 37° C. for 30 minutes to form a gel layer. Transfected cells (~$10^4$ cells/well) were seeded on to the Matrigel-coated 24-well plates and cultured in Ham's F-12K medium containing 10% FCS for 4 hr. Tube formation was recorded with phase contrast microscopy. Images were captured using a Scion digital camera and analyzed using Imaging J software.

Statistical Analysis

Results were presented as mean±standard deviation. Statistical significance was assessed by ANOVA with post-hoc paired testing of parametric data (n=3 for all statistical analyses). A value of $p<0.05$ was considered to be statistically significant.

Results

Suppression of p22phox Gene Expression and ROS Generation by sip22phox

Figure 2:
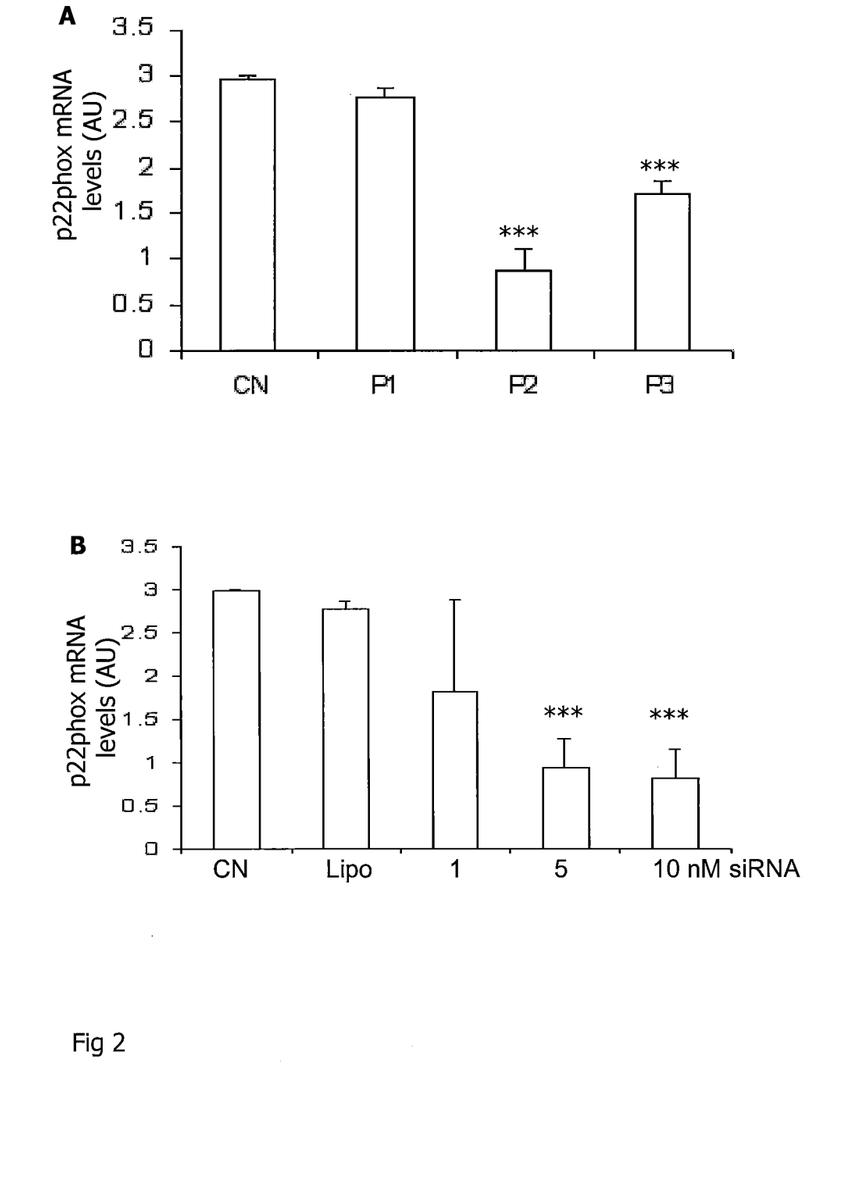
FIG. 2. Quantification of mRNA levels of p22phox transfected with siRNAs against three target sites (FIG. 2A) or a dose response curve (FIG. 2B) in human ECs. Total RNAs were prepared ~24 hrs after transfection with siRNAs. To determine the efficiencies of suppression of p22phox mRNA levels, siRNAs against three target sites (P1, P2, P3, FIG. 1A) were used to transfect human ECs (at 10 nmol/L). *p<0.001.

Among the three siRNAs synthesised for targeting against three difference fragments of the p22phox mRNA sequence, a sip22phox against the first target sequence had little effect in knocking down p22phox mRNA levels (P1, FIG. 2A). A sip22phox against the second site (P2, FIG. 2A) suppressed p22phox by ~70% (P2, $p<0.001$, FIG. 2A), and a sip22phox targeting the third sequence suppressed p22phox by ~42% ($p<0.001$, FIG. 2A). There was ~68% reduction in p22phox mRNA levels 24 hrs after transfection with sip22phox (P2) at 5 nmol/L and ~72% reduction at 10 nmol/L concentrations (FIG. 2B, $p<0.001$). In contrast, Lipofectamine had no significant effects on p22phox mRNA levels (FIG. 2B). Similarly, the inventors measured mRNA levels of 18S rRNA and did not observe any difference in 18S rRNA 24 hrs post-transfection with 1, 5, and 10 nM sip22phox (data not shown). Thus, the sip22phox targeting the second site (sequences: 5'-AAG CAC ATG ACC GCC GTG GTG-3' (sense) (SEQ ID NO:2) and 5'-AAC ACC ACG GCG GTC ATG TGC-3' (antisense) (SEQ ID NO:3)) was used for all subsequent studies.

Figure 3:
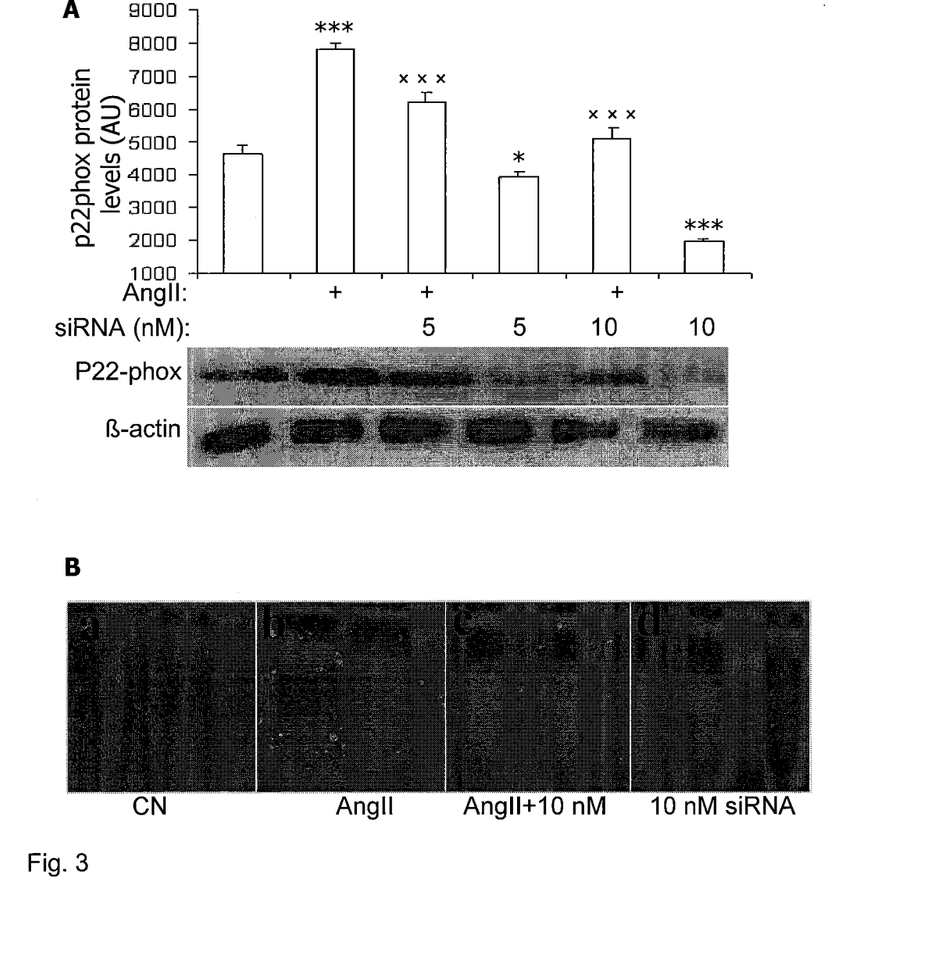

To further establish the potency of sip22phox in knocking down p22phox expression, p22phox protein levels were measured and Ang II was used as a positive control in this study, as Ang II increases vascular p22phox expression[42]. As expected, Ang II (at 1 µmol/L) increased p22phox protein levels in ECs (by ~69%: FIG. 3A, $p<0.001$). Consistent with mRNA data, there were ~15% (p=0.018, FIG. 3A) and ~58% ($p<0.001$, FIG. 3A) reductions in p22phox protein levels in cells treated with sip22phox at 5 nmol/L and 10 nmol/L respectively. In the presence of Ang II, the sip22phox reduced p22phox protein levels by ~20% at 5 nmol/L ($p<0.001$, Ang II+5 nmol/L siRNA vs. Ang II, FIG. 3A), and by ~35% at 10 nmol/L ($p<0.001$, Ang II+10 nmol/L siRNA vs. Ang II, FIG. 3A), and the increase in p22phox protein levels stimulated by Ang II was almost blocked by treatment with sip22phox at 10 nmol/L (p=0.10, Ang II+10 nmol/L siRNA vs. CN). These data showed that sip22phox not only reduced p22phox protein levels, but also antagonised the stimulatory effects of Ang II, despite a high Ang II concentration.

ROS production was estimated by assessment with the oxidative fluorescent dye dihydroethidium (DHE). As expected, ROS production was stimulated by Ang II, whereas sip22phox reduced ROS generation either in the presence of Ang II or without Ang II (FIG. 3B).

Effect of Knocking Down p22phox on Angiogenesis in ECs

The inventors then determined the functional efficacy of sip22phox through studies of angiogenesis and key parameters (adhesion, proliferation, migration and vascular tube formation) relevant to angiogenesis in ECs.

Figure 4:
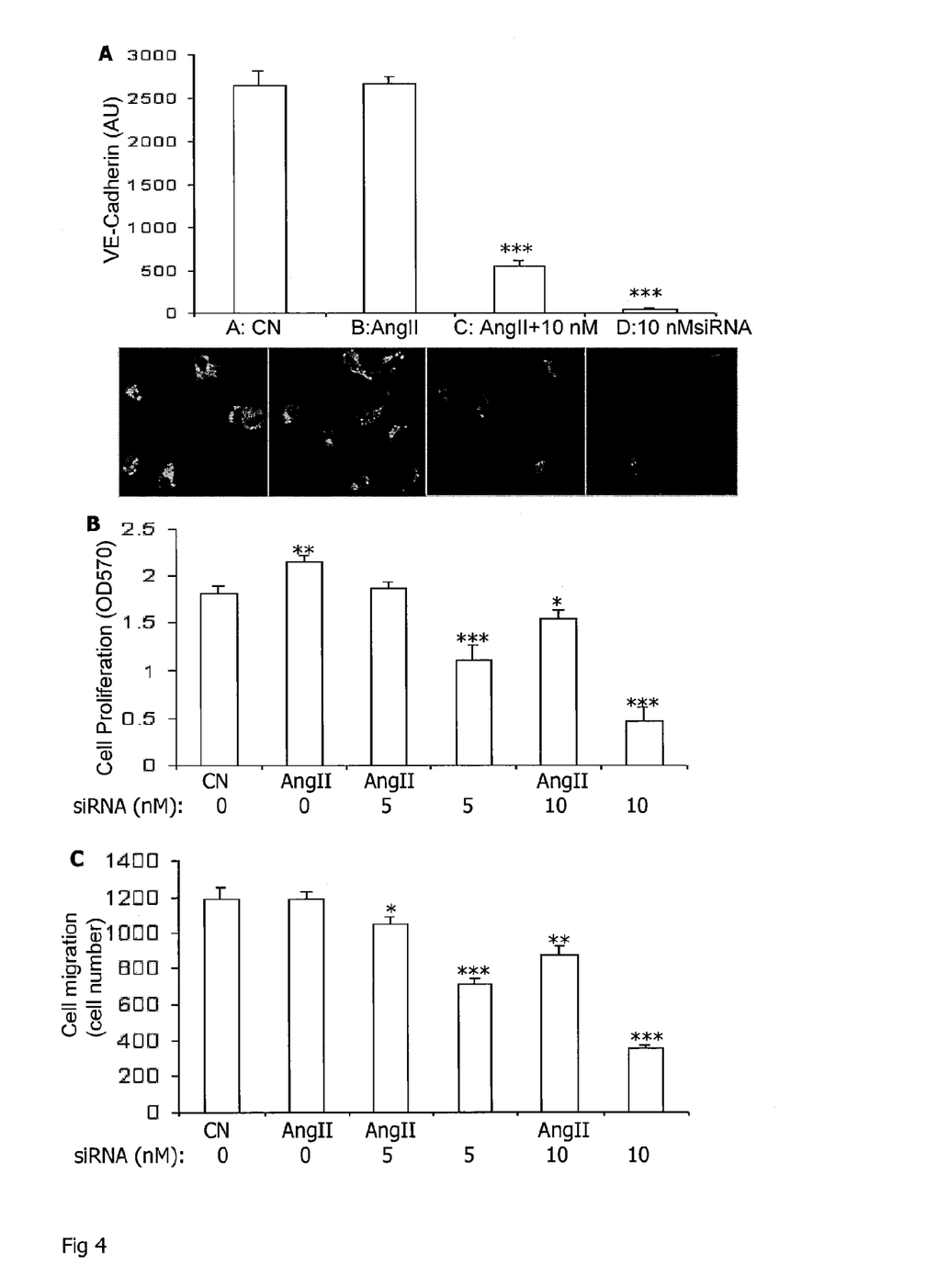
FIG. 4. Analysis of angiogenic parameters in ECs.

The cell proliferation rate as measured with MTT was reduced by ~39% ($p<0.001$) and ~75% ($p<0.001$) with sip22phox at 5 and 10 nmol/L respectively (FIG. 4B). Ang II per se stimulated ECs proliferation by ~48% (Ang II vs. CN, $p<0.01$; FIG. 4B). The stimulatory effect of Ang II was blocked with 5 nmol/L sip22phox in ECs (Mg II+5 nmol/L siRNA vs. CN, p=0.26; FIG. 4B), and a reduced cell proliferation rate was observed (by ~14%) with sip22phox at 10 nmol/L (Mg II+10 nmol/L siRNA vs. CN, $p<0.05$, FIG. 4B). These data established the potency in the reduction of cell proliferation through knocking down p22phox.

VE-cadherin is an endothelial-specific cadherin localized at intercellular junctions[43], and involved in EC migration[43], contact-induced growth inhibition[44] and endothelial cell assembly into tubular structures[45]. The sip22phox at 10 nmol/L markedly reduced expression of VE-cadherin by ~98% ($p<0.0001$, FIG. 4A) or by ~79% in the presence of Ang II ($p<0.001$, FIG. 4A). However, Mg II did not affect VE-cadherin expression in EC cells.

The sip22phox reduced EC migration as measured using the Matrigel migration chamber, by ~26% ($p<0.001$) and ~70% respectively ($p<0.001$; FIG. 4C) at 5 and 10 nmol/L. Although Ang II per se had no significant effects on EC migration (p=0.97, FIG. 4C), sip22phox reduced EC migration by ~13% and ~26% ($p<0.05$ and $p<0.01$ respectively, FIG. 4C) at 5 or 10 nmol/L in the presence of Ang II. Thus, although Ang II per se did not affect VE-cadherin or EC migration, the effects of sip22phox on VE-cadherin and EC migration can be partly antagonised with high dose of Ang II.

The inventors then evaluated the effects of sip22phox on angiogenesis in human umbilical vein endothelial cells.

Figure 5:
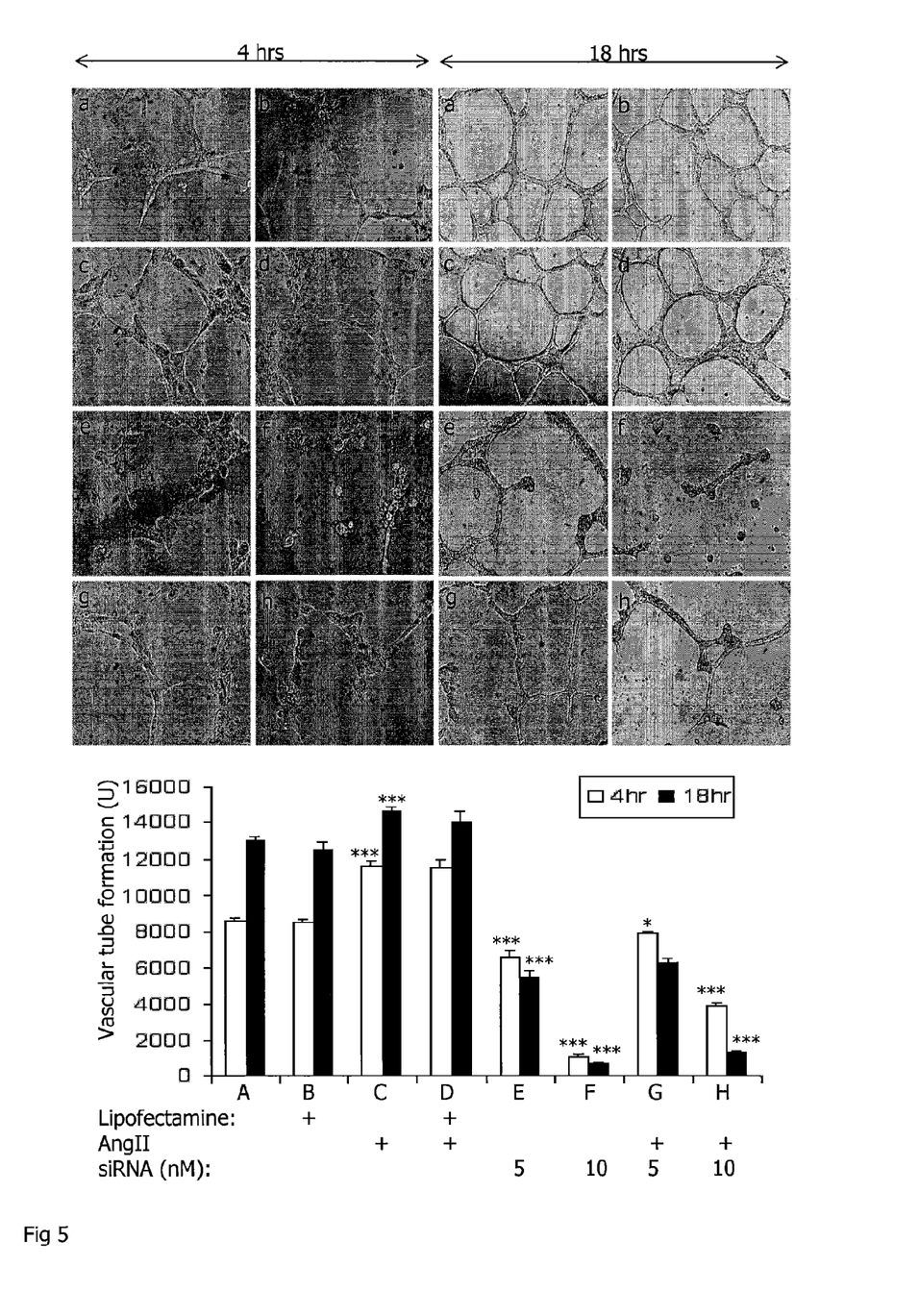

Lipofectamine had no effects on angiogenesis either on its own or in the presence of Ang II at both 4 and 18 hrs (FIG. 5b). Ang II increased vascular tube formation by ~35% ($p<0.001$) at 4 hrs or by ~13% at 18 hrs ($p<0.001$, FIG. 5c, d). The sip22phox at 5 nmol/L reduced vascular tube formation by ~23% at 4 hrs and by ~57% at 18 hr (FIG. 5e, $p<0.001$). The sip22phox at 10 nmol/L reduced vascular tube formation by ~87% at 4 hrs and by ~94% (at 10 nmol/L, $p<0.001$ for all differences, FIG. 5f) at 18 hrs. Furthermore, sip22phox at 5 nmol/L blocked enhancement of vascular tube formation by Ang II (FIG. 5g) and there was a further reduction in tube formation in cells treated with 10 nmol/L sip22phox in the presence of Ang II at either 4 hrs (by ~45%) or 18 hrs (by ~90%, $p<0.001$; FIG. 5h). Thus, the effects of sip22phox on angiogenesis were extremely potent, as almost all angiogenesis was blocked by addition of 10 nmols/L sip22phox, despite the presence of Ang II.

p22phox on ECs Apoptosis and their Key Survival Signal Transduction Pathways

To investigate the potential mechanisms underlying reduced vascular tube formation due to knocking down p22phox with siRNAs, we determined the effects of sip22phox on Akt phosphorylation, a key molecule involved in EC migration and proliferation[3, 17, 46].

Figure 6:
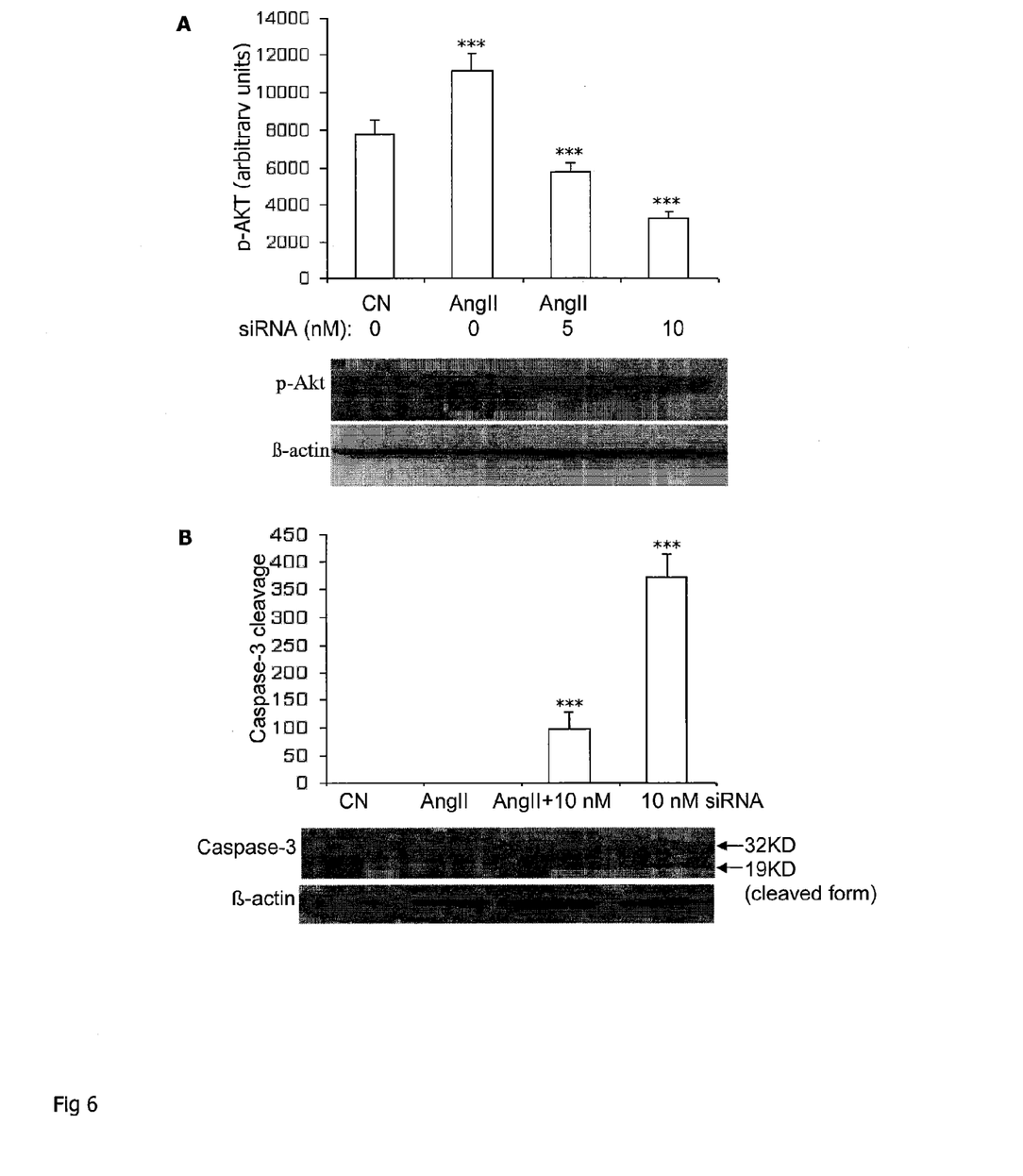

Ang II stimulated Akt phosphorylation by ~44% (p<0.001, FIG. 6A). The increased phosphorylation of Akt stimulated by Ang II was blocked by sip22phox at 5 nmol/L and Akt phosphorylation was reduced by ~58% in ECs treated with sip22phox at 10 nmol/L (p<0.001, FIG. 6A).

To determine whether the apoptosis signalling pathway was affected in reduced vascular tube formation due to knocking down p22phox, caspase-3 cleavage (19 KD product, FIG. 6B) was measured. Caspase-3 is a key mediator of apoptosis, and cleavage of this enzyme to its active form correlates with the onset of apoptosis[47]. Ang II per se had no significant effect on caspase-3 cleavage in ECs (FIG. 6B). However, there was a marked increase in caspase-3 cleavage in ECs treated with siRNA against p22phox despite the presence of Ang II. There was also a further ~3 fold increase in caspase-3 cleavage in ECs treated with sip22phox in the absence of Ang II (FIG. 6B).

Discussion

The inventors have shown that: 1) one of the 3 siRNAs designed against the human NADPH oxidase subunit p22phox (sip22phox) was effective in knocking expression and functions of p22phox in human ECs, as almost all angiogenesis was blocked by addition of only 10 mmol/L of sip22phox; 2) sip22phox markedly suppressed basal and Ang II stimulated angiogenesis in human ECs, suggesting a critical role of p22phox signalling in angiogenesis; 3) expression of VE-cadherin was markedly lower in human ECs with p22phox knocked down, suggesting a novel pathway between p22phox and VE-cadherin.

SiRNAs suppress gene function through base pairing with the target mRNA molecules, via an RNA interference mechanism[48, 49]. However, although all 3 siRNAs designed in this study form perfect matches with the p22phox mRNA coding sequence, the magnitude of knocking down of p22phox by siRNAs varied depending on the region targeted by a siRNA. In these studies, the P1 sequence had little effect whereas the P2 sequence (sip22phox) had a major effect in knocking down p22phox mRNA and protein levels. Similar results have been reported in siRNAs targeting different mRNA transcripts[50,51]. For example, out of 14 siRNAs designed to target the human telomerase reverse transcriptase, 5 siRNAs have almost no effects[51]. Thus, it is very important to confirm effective sequence targeting against a given mRNA transcript.

RNAi-based gene silencing can be highly specific, as evidenced by selective silencing of alleles containing single nucleotide polymorphisms[52]. A commercially available scrambled siRNA has been used as negative control to determine whether the effects of knocking down the target mRNA transcripts are specific to the designed siRNA. The inventors did not use scrambled siRNAs as additional negative controls for two reasons. Firstly one of the specific siRNA sequences (P1) had little effect on p22phox expression. Secondly they have observed in a previous study that scrambled siRNA can generate off-target effects (e.g. induction of adipocyte differentiation[53]). The off-target effects of siRNAs against specific mRNA have been observed in other studies[54]. The off-target effects of siRNA are generated due to the complementarity between siRNA sequence at position 2-8 heptamer and the "seed" sequence in the 3'UTR of the mRNA transcripts[55]. Off target effects of siRNA can be minimised through chemical modifications of the siRNA backbone[56]. The primary aim this study was to determine functional effects of sip22phox.

ROS at low concentrations can act as signalling molecules and are involved in EC proliferation and migration, which may contribute to angiogenesis[3, 13-16]. P22phox, as an integral component of NADPH oxidase, is critically involved in ROS generation in endothelial cells. The data showing that knocking down of p22phox reduces ROS generation in human ECs is consistent with data from studies using VSMC[21] and cultured ECs derived from porcine aorta[57]. This is consistent with the observation in transgenic mice that over-expression of p22phox in smooth muscle cells elevates generation of ROS[58]. In this study the inventors have further demonstrated that knocking down p22phox markedly reduces vascular tube formation in human ECs, with parallel reduction in Akt phosphorylation and activation of caspase-3. This supports previous work suggesting a key role of background ROS generation in signalling pathways for angiogenesis[59].

Phosphoinositide 3-kinase (PI3-K) and its downstream serine/threonine kinase Akt/protein kinase B play a central role in promoting the survival of a wide range of cells including ECs[46]. Three isoforms of Akt (Akt1, Akt2 and Akt3) have been reported. Akt1 (referred to as Akt in this study) is predominantly expressed in ECs and plays a crucial role in angiogenesis[46, 60]. Akt knockout mice demonstrate growth retardation and elevated apoptosis[61, 62]. The data showing that knocking down p22phox expression reduced Akt phosphorylation in parallel to decreasing vascular tube formation, suggest that Akt phosphorylation may be involved in p22phox regulated angiogenesis.

Caspase-3 is a key molecule involved in apoptosis[63], and cleavage of this enzyme to its active form correlates with the onset of apoptosis. The active-site cysteine residue is susceptible to oxidation, resulting in caspase inactivation and thus potentially inhibition of apoptosis, which is illustrated by the findings that ROS such as $H_2O_2$ can both induce[64-66] and inhibit apotosis[66-68]. The data showing that knocking down p22phox reduces ROS generation and markedly increases caspase-3 activation, suggest that basal activity of p22phox (hence ROS generation) may be important in suppressing caspase-3 activation.

These data provide direct evidence indicating that basal expression of p22phox is required for vascular tube formation in human ECs. The data obtained in human ECs are consistent with previous studies in mice in which over-expression of p22phox in smooth muscle cells resulted in stimulation angiogenesis[58]. Interestingly, the inventors' data showing that Ang II upregulates in human ECs both p22phox protein expression and ROS generation, is consistent with a report showing that stimulation by Ang II of NADPH oxidase activity in human ECs is regulated by enhanced binding of p47phox to p22phox[33]. The findings are also consistent with findings of an in vivo study showing that AngII infusion increases p22phox mRNA and protein levels in the renal cortex in rats[69], and that the expression of p22phox can be knocked down by siRNA against p22phox in rats[69]. In this regard, Ang II can have similar effects to over expression of p22phox. The inventors further show that Ang II induced cell proliferation, AKT phosphorylation and vascular tube formation are antagonised by sip22phox in human ECs, supporting the notion that the effects of Ang II are mediated at least in part, through p22phox[25]. Although Ang II per se does not have stimulatory effects on cell migration, VE cadherin expression and caspase 3 activation, as shown in this study, sip22phox has dose dependent effects on reduction of cell migration, VE-cadherin expression, caspase 3 activation and vascular tube formation. These data suggest that the effects of p22phox can occur independent of Ang II. However, Ang II can also antagonise the effects of sip22phox on cell migration, expression of VE-cadherin and activation of caspase 3, suggesting interactions between Ang II signalling pathways and NADPH oxidase pathways.

VE-cadherin is an endothelial-specific cadherin localized at intercellular junctions[43], and is an important mediator in angiogenesis. VE-cadherin is critically involved in the maintenance of the integrity of the endothelium[70], EC migration[43], contact-induced growth inhibition[44] and most notably, endothelial cell assembly into tubular structures[45]. Tumour necrosis factor (TNF-α) caused tyrosine phosphorylation of VE-cadherin, which appears to be regulated by intracellular oxidant production through endothelial NAD(P)H oxidase, as antioxidants and expression of a transdominant inhibitor of the NADPH oxidase, p67phox, effectively block the effects of TNF-α on all 3 parameters of junctional integrity[71]. The novel data showing that suppression of p22phox by siRNA markedly reduces expression of VE-cadherin is consistent with the view that VE-cadherin expression may be mediated by ROS generation. More studies are needed to explore further mechanisms underlying reduced VE-cadherin expression caused by sip22phox.

Therefore, the inventors' data have provided convincing evidence showing that sip22phox can effectively knock down p22phox expression and function in human ECs. The studies provide a new siRNA tool for understanding the role of p22phox and NADPH oxidase in pathophysiology and in mechanisms for efficacy. The findings clearly also suggest the need for further work to explore the therapeutic potential of sip22phox. siRNAs are a potential new class of drugs with the advantage of high specificity and high potency (effective with nanomolar levels), which is at least 100-fold greater than that of anti-sense RNA (which usually requires microM levels).

Potential applications of sip22phox include any pathophysiological setting in which activity of NAD(P)H oxidase adversely affects cell-signalling. Particular examples of possible applications concern angiogenesis and modulation of oxidant stress generation, for example, to suppress tumour angiogenesis[17], an anti-angiogenic approach to atheromatous plaque stabilisation[72] and reduction in abnormal blood vessel formation in diabetes mellitus in retinal, renal and other circulations. Other therapeutic areas of interest include a wide range of infective and inflammatory disorders, neoplastic disease and both systemic and neuro-degenerative disorders.

Anti-tumour therapy with sip22phox is promising as evidenced by the inventors' data showing that sip22phox can block angiogenesis both on its own, and by antagonising the effects of Ang II. Of note, inhibition of angiogenesis with an Angiotensin II Type 1 receptor blocker has been linked with reduced tumour formation in a number of studies[73-76].

NADPH oxidase is recognized to be a major contributor to the oxidative stress implicated in endothelial injury, intimal hyperplasia, remodelling and stenosis or restenosis[12] in bypass grafts or at sites of primary angioplasty and stenting[77-79]. The inventors anticipate that sip22phox treatment may reduce the occurrence of early ischaemic syndromes after bypass grafting or primary angioplasty and may be clinically useful in helping to prevent or reduce later in-stent restenosis and bypass graft stenosis.

Thus, the inventors are convinced from the consistent data in the present studies that they have identified a potent sip22phox with efficacy in knocking down expression and function of p22phox. They have also shown that constitutive expression of p22phox is required for vascular tube formation in human endothelial cells.

REFERENCES

1. Kiefer F N, Neysari S, Humar R, Li W, Munk V C, Battegay E J. Hypertension and angiogenesis. Curr Pharm Des. 2003; 9:1733-1744.
2. Hanahan D, Folkman J. Patterns and emerging mechanisms of the angiogenic switch during tumorigenesis. Cell. 1996; 86:353-364.
3. Ushio-Fukai M. Redox signaling in angiogenesis: Role of NADPH oxidase. Cardiovas Res. 2006; 71:226-235.
4. Black M J, Bertram J F, Johnston C I. Effect of angiotensin-converting enzyme inhibition on myocardial vascularization in the adolescent and adult spontaneously hypertensive rat. J. Hypertens. 2001; 19:785-794.
5. Piadys P, Senniaub F, Brault S, Checchin D, Lahaie I, Le N L, Bibeau K, Carnbonie G, Abran D, Brochu M, Thibault G, Hardy P, Chemtob S, Nuyt A M. Microvascular rarefaction and decreased angiogenesis in rats with fetal programming of hypertension associated with exposure to a low-protein diet in utero. Am J Physiol Regul Integr Comp Physiol. 2005; 289:R1580-1588.
6. Hughes A D, Martinez-Perez E, Jabbar A S, Hassan A, Witt N R, Mistry P D, Chapman N, Stanton A V, Beevers G, Pedrinelli R, Parker K H, Thom S A. Quantification of topological changes in retinal vascular architecture in essential and malignant hypertension. J Hypertens. 2006; 24:889-894.
7. Poston L. Influences of maternal nutritional status on vascular function in the offspring. Current drug targets. 2007; 8:914-922.
8. Antonios T F, Singer D R, Markandu N D, Mortimer P S, MacGregor G A. Rarefaction of skin capillaries in borderline essential hypertension suggests an early structural abnormality. Hypertension. 1999; 34:655-658.
9. Noon J P, Walker B R, Webb D J, Shore A C, Holton D W, Edwards H V, Watt G C. Impaired microvascular dilatation and capillary rarefaction in young adults with a predisposition to high blood pressure. J Clin Invest. 1997; 99:1873-1879.
10. Hasan K M, Manyonda I T, Ng F S, Singer D R, Antonios T F. Skin capillary density changes in normal pregnancy and pre-eclampsia. J Hypertens. 2002; 20:2439-2443.
11. Antonios T F. Microvascular Rarefaction in Hypertension—Reversal or Over-Correction by Treatment? Am J Hypertens. 2006; 19:484-485.
12. Griendling K K, Sorescu D, Ushio-Fukai M. NAD(P)H oxidase: role in cardiovascular biology and disease. Circ Res. 2000; 86:494-501.
13. Chen H C, Stone S J, Zhou P, Buhman K K, Farese R V, Jr. Dissociation of obesity and impaired glucose disposal in mice overexpressing acyl coenzyme a:diacylglycerol acyltransferase 1 in white adipose tissue. Diabetes. 2002; 51:3189-3195.
14. Ushio-Fukai M, Tang Y, Fukai T, Dikalov S I, Ma Y, Fujimoto M, Quinn M T, Pagano P J, Johnson C, Alexander R W. Novel role of gp91(phox)-containing NAD(P)H oxidase in vascular endothelial growth factor-induced signaling and angiogenesis. Circ Res. 2002; 91:1160-1167.
15. Tojo T, Ushio-Fukai M, Yamaoka-Tojo M, Ikeda S, Patrushev N, Alexander R W. Role of gp91phox (Nox2)-containing NAD(P)H oxidase in angiogenesis in response to hindlimb ischemia. Circulation. 2005; 111:2347-2355.
16. Boden G, Chen X. Effects of fat on glucose uptake and utilization in patients with non-insulin-dependent diabetes. J Clin Invest 1995; 96:1261-1268.
17. Ushio-Fukai M, Alexander R W. Reactive oxygen species as mediators of angiogenesis signaling: role of NAD(P)H oxidase. Mol Cell Biochem. 2004; 264:85-97.
18. Li J M, Shah A M. Intracellular localization and preassembly of the NADPH oxidase complex in cultured endothelial cells. J Biol Chem. 2002; 277:19952-19960.

19. Ray R, Shah A M. NADPH oxidase and endothelial cell function. *Clin Sci (Lond)*. 2005; 109:217-226.
20. Griendling K K, Sorescu D, Ushio_Fukai M. NAD(P)H oxidase: role in cardiovascular biology and disease. *Circ Res*. 2000; 86:494-501.
21. Ushio-Fukai M, Zafari A M, Fukui T, Ishizaka N, Griendling K K. p22phox Is a Critical Component of the Superoxide-generating NADH/NADPH Oxidase System and Regulates Angiotensin II induced Hypertrophy in Vascular Smooth Muscle Cells. *J. Biol. Chem.* 1996; 271:23317-23321.
22. Lassegue B, Clempus R E. Vascular NAD(P)H oxidases: specific features, expression, and regulation. *Am J Physiol Regul Integr Comp Physiol.* 2003; 285:R277-297.
23. Rajagopalan S, Kurz S, Munzel T, Tarpey M, Freeman B A, Griendling K K, Harrison D G. Angiotensin II-mediated Hypertension in the Rat Increases Vascular Superoxide Production via Membrane NADH/NADPH Oxidase Activation. Contribution to Alterations of Vasomotor Tone. *J Clin Invest* 1996; 97:1916-1923.
24. Fukui T, Ishizaka N, Rajagopalan S, Laursen J B, Capers Qt, Taylor W R, Harrison D G, de Leon H, Wilcox J N, Griendling K K. p22phox mRNA expression and NADPH oxidase activity are increased in aortas from hypertensive rats. *Circ Res.* 1997; 80:45-51.
25. Modlinger P, Chabrashvili T, Gill P S, Mendonca M, Harrison D G, Griendling K K, Li M, Raggio J, Wellstein A, Chen Y, Welch W J, Wilcox C S. RNA silencing in vivo reveals role of p22phox in rat angiotensin slow pressor response. *Hypertension*. 2006; 47:238-244.
26. Zalba G, San Jose G, Moreno M U, Fortuno A, Diez J. NADPH oxidase-mediated oxidative stress: genetic studies of the p22(phox) gene in hypertension. *Antioxid Redox Signal* 2005; 7:1327-1336.
27. Kim K I, Na J E, Kang S Y, Cho Y S, Choi D J, Kim C H, Kim H S, Oh B H, Choi Y H, Kwon I S, Park S C. Impact of NAD(P)H oxidase p22(phox) gene polymorphism on vascular aging in Korean centenarian and nonagenarian. *Int J Cardiol.* 2007.
28. Hayaishi-Okano R, Yamasaki Y, Kajimoto Y, Sakamoto K, Ohtoshi K, Katakami N, Kawamori D, Miyatsuka T, Hatazaki M, Hazama Y, Hori M. Association of NAD(P)H oxidase p22 phox gene variation with advanced carotid atherosclerosis in Japanese type 2 diabetes. *Diabetes Care*. 2003; 26:458-463.
29. Hayaishi-Okano R, Yamasaki Y, Ohtoshi K, Yasuda T, Katakami N, Hirano T, Yoshino G, Kajimoto Y, Hori M. NAD (P)H oxidase p22 phox C242T polymorphism affects LDL particle size and insulin resistance in Japanese subjects. *J Atheroscler Thromb.* 2002; 9:200-205.
30. He M A, Cheng L X, Jiang C Z, Zeng H S, Wang J, Wang F, Chen Y, Yang M, Tan H, Zheng H Y, Hu F B, Wu T C. Associations of polymorphism of P22(phox) C242T, plasma levels of vitamin E, and smoking with coronary heart disease in China. *Am heart J* 2007; 153:640 e641-646.
31. Djordjevic T, Pogrebniak A, BelAiba R S, Bonello S, Wotzlaw C, Acker H, Hess J, Gorlach A. The expression of the NADPH oxidase subunit p22phox is regulated by a redox-sensitive pathway in endothelial cells. *Free Rad Biol & Med* 2005; 38:616-630.
32. Yamagishi S, Nakamura K, Ueda S, Kato S, Imaizumi T. Pigment epithelium-derived factor (PEDF) blocks angiotensin II signaling in endothelial cells via suppression of NADPH oxidase: a novel anti-oxidative mechanism of PEDF. *Cel Tis Res* 2005; 320:437-445.
33. Li J M, Shah A M. Mechanism of endothelial cell NADPH oxidase activation by angiotensin II. Role of the p47phox subunit. *J Biol Chem.* 2003; 278:12094-12100.
34. Matsumoto T, Claesson-Welsh L. VEGF receptor signal transduction. *Sci STKE.* 2001; 2001:RE21.
35. de Fougerolles A, Vornlocher H-P, Maraganore J, Lieberman J. Interfering with disease: a progress report on siRNA-based therapeutics. *Nat Rev Drug Discov.* 2007; 6:443-453.
36. Scherer L, Rossi J J, Weinberg M S. Progress and prospects: RNA-based therapies for treatment of HIV infection. *Gene Ther.* 14:1057-1064.
37. Cai H, Griendling K K, Harrison D G. The vascular NAD(P)H oxidases as therapeutic targets in cardiovascular diseases. *Tr Pharmaco Sci.* 2003; 24:471-478.
38. Shizukuda Y, Tang S, Yokota R, Ware J A. Vascular endothelial growth factor-induced endothelial cell migration and proliferation depend on a nitric oxide-mediated decrease in protein kinase C delta activity. *Circ Res.* 1999; 85:247-256.
39. Zhou X, Murphy F R, Gehdu N, Zhang J, Iredale J P, Benyon R C. Engagement of {alpha} v {beta}3 Integrin Regulates Proliferation and Apoptosis of Hepatic Stellate Cells. *J. Biol. Chem.* 2004; 279:23996-24006.
40. Xu Y, Mirmalek-Sani S, Yang X, Zhang J, Oreffo R O C. Small Interfering RNA (siRNA) against Peroxisome Proliferators-Activated Receptors Gamma (PPARγ) Suppresses Adipocyte Differentiation from Human Preadipocytes and Fetal-derived Mesenchymal Cells. *Exp Cell Res.* 2006; 312:1856-1864.
41. Mosmann T. Rapid colorimetric assay for cellular growth and survival: application to proliferation and cytotoxicity assays. *J Immunol Methods.* 1983; 65:55-63.
42. Sarr M, Chataigneau M, Martins S, Schott C, El Bedoui J, Oak M H, Muller B, Chataigneau T, Schini-Kerth V B. Red wine polyphenols prevent angiotensin II-induced hypertension and endothelial dysfunction in rats: role of NADPH oxidase. *Cardiovasc Res.* 2006; 71:794-802.
43. Breviario F, Caveda L, Corada M, Martin-Padura I, Navarro P, Golay J, Introna M, Gulino D, Lampugnani M G, Dejana E. Functional properties of human vascular endothelial cadherin (7B4/cadherin-5), an endothelium-specific cadherin. *Arterioscler Thromb Vasc Biol.* 1995; 15:1229-1239.
44. Caveda L, Martin-Padura I, Navarro P, Breviario F, Corada M, Gulino D, Lampugnani M G, Dejana E. Inhibition of cultured cell growth by vascular endothelial cadherin (cadherin-5/VE-cadherin). *J Clin Invest.* 1996; 98:886-893.
45. Bach T L, Barsigian C, Chalupowicz D G, Busier D, Yaen C H, Grant D S, Martinez J. VE-Cadherin mediates endothelial cell capillary tube formation in fibrin and collagen gels. *Exp Cell Res.* 1998; 238:324-334.
46. Somanath P R, Razorenova O V, Chen J, Byzova T V. Akt1 in endothelial cell and angiogenesis. *Cell cycle* (Georgetown, Tex. 2006; 5:512-518.
47. Thornberry N A, Lazebnik Y. Caspases: enemies within. *Science.* 1998; 281:1312-1316.
48. Fire A, Xu S, Montgomery M K, Kostas S A, Driver S E, Mello C C. Potent and specific genetic interference by double-stranded RNA in Caenorhabditis elegans. *Nature.* 1998; 391:806-811.
49. Couzin J. BREAKTHROUGH OF THE YEAR: Small RNAs Make Big Splash. *Science.* 2002; 298:2296-2297.
50. Harborth J, Elbashir S M, Vandenburgh K, Manning a H, Scaringe S A, Weber K, Tuschl T. Sequence, chemical, and structural variation of small interfering RNAs and short 50. hairpin RNAs and the effect on mammalian gene silencing. *Anti & Nuc Acid Drug Dev.* 2003; 13:83-105.
51. Gandellini P, Folini M, Bandiera R, De Cesare M, Binda M, Veronese S, Daidone M G, Zunino F, Zaffaroni N. Down-regulation of human telomerase reverse transcriptase through specific activation of RNAi pathway quickly results in cancer cell growth impairment. *Biochem Pharmacol.* 2007; 73:1703-1714.
52. Schwarz D S, Ding H, Kennington L, Moore J T, Schelter J, Burchard J, Linsley P S, Aronin N, Xu Z, Zamore P D. Designing siRNA that distinguish between genes that differ by a single nucleotide. *PLoS Genet.* 2006; 2:e140.
53. Yunhe Xu S-HM-S, Feng Lin, Junlong Zhang and Richard O. C. Oreffo. Adipogenic induction using negative small interfering RNA in human fetal mesenchymal stem cells *RNA.* 2007; 13:1179-1183.
54. Pei Y, Tuschl T. On the art of identifying effective and specific siRNAs. *Nat Methods.* 2006; 3:670-676.
55. Birmingham A, Anderson E M, Reynolds A, Ilsley-Tyree D, Leake D, Fedorov Y, Baskerville S, Maksimova E, Robinson K, Karpilow J, Marshall W S, Khvorova A. 3[prime] UTR seed matches, but not overall identity, are associated with RNAi off-targets. *Nat Meth.* 2006; 3:199-204.
56. Jackson A L, Burchard J, Leake D, Reynolds A, Schelter J, Guo J, Johnson J M, Lim L, Karpilow J, Nichols K, Marshall W, Khvorova A, Linsley P S. Position-specific chemical modification of siRNAs reduces "off-target" transcript silencing. *RNA.* 2006; 12:1197-1205.
57. Schafer M, Schafer C, Ewald N, Piper H M, Noll T. Role of redox signaling in the autonomous proliferative response of endothelial cells to hypoxia. *Circ Res.* 2003; 92:1010-1015.
58. Khatri J J, Johnson C, Magid R, Lessner S M, Laude K M, Dikalov S I, Harrison D G, Sung H J, Rong Y, Galis Z S. Vascular oxidant stress enhances progression and angiogenesis of experimental atheroma. *Circulation.* 2004; 109: 520-525.
59. Ushio-Fukai M, Tang Y, Fukai T, Dikalov S I, Ma Y, Fujimoto M, Quinn M T, Pagano P J, Johnson C, Alexander R W. Novel role of gp91(phox)-containing NAD(P)H oxidase in vascular endothelial growth factor-induced signaling and angiogenesis. *Circ Res.* 2002; 91:1160-1167.
60. Chen J, Somanath P R, Razorenova O, Chen W S, Hay N, Bornstein P, Byzova T V. Akt1 regulates pathological angiogenesis, vascular maturation and permeability in vivo. *Nat Med.* 2005; 11:1188-1196.
61. Cho H, Thorvaldsen J L, Chu Q, Feng F, Birnbaum M J. Akt1/PKBalpha is required for normal growth but dispensable for maintenance of glucose homeostasis in mice. *J Biol Chem.* 2001; 276:38349-38352.
62. Chen W S, Xu P Z, Gottlob K, Chen M L, Sokol K, Shiyanova T, Roninson I, Weng W, Suzuki R, To be K, Kadowaki T, Hay N. Growth retardation and increased apoptosis in mice with homozygous disruption of the Akt1 gene. *Gen & Dev* 2001; 15:2203-2208.
63. Yuan J, Horvitz H R. A first insight into the molecular mechanisms of apoptosis. *Cell.* 2004; 116:S53-56, 51 p following S59.
64. Skulachev V P. Cytochrome c in the apoptotic and antioxidant cascades. *FEBS Lett.* 1998; 423:275-280.
65. Jabs T. Reactive oxygen intermediates as mediators of programmed cell death in plants and animals. *Biochem Pharmacol.* 1999; 57:231-245.
66. Samali A, Nordgren H, Zhivotovsky B, Peterson E, Orrenius S. A comparative study of apoptosis and necrosis in HepG2 cells: oxidant-induced caspase inactivation leads to necrosis. *Biochem Biophys Res Commun.* 1999; 255:6-11.
67. Hampton M B, Orrenius S. Dual regulation of caspase activity by hydrogen peroxide: implications for apoptosis. *FEBS Lett.* 1997; 414:552-556.
68. Lee Y J, Shacter E. Oxidative stress inhibits apoptosis in human lymphoma cells. *J Biol Chem.* 1999; 274:19792-19798.
69. Modlinger P, Chabrashvili T, Gill P S, Mendonca M, Harrison D G, Griendling K K, Li M, Raggio J, Wellstein A, Chen Y, Welch W J, Wilcox C S. RNA Silencing In Vivo Reveals Role of p22phox in Rat Angiotensin Slow Pressor Response. *Hypertension* 2006; 47:238-244.
70. Gulino D, Delachanal E, Concord E, Genoux Y, Morand B, Valiron M-O, Sulpice E, Scaife R, Alemany M, Vernet T. Alteration of Endothelial Cell Monolayer Integrity Triggers Resynthesis of Vascular Endothelium Cadherin. *J. Biol. Chem.* 1998; 273:29786-29793.
71. Nwariaku F E, Liu Z, Zhu X, Nahari D, Ingle C, Wu R F, Gu Y, Sarosi G, Terada L S. NADPH oxidase mediates vascular endothelial cadherin phosphorylation and endothelial dysfunction. *Blood* 2004; 104:3214-3220.
72. Jain R K, Finn A V, Kolodgie F D, Gold H K, Virmani R. Antiangiogenic therapy for normalization of atherosclerotic plaque vasculature: a potential strategy for plaque stabilization. *Nat Clin Pract* 2007; 4:491-502.
73. Deshayes F, Nahmias C. Angiotensin receptors: a new role in cancer? *Trends Endocrinol Metab.* 2005; 16:293-299.
74. Egami K, Murohara T, Shimada T, Sasaki K, Shintani S, Sugaya T, Ishii M, Akagi T, Ikeda H, Matsuishi T, Imaizumi T. Role of host angiotensin II type 1 receptor in tumor angiogenesis and growth. *J Clin Invest.* 2003; 112:67-75.
75. Sanders P M, Russell S T, Tisdale M I Angiotensin II directly induces muscle protein catabolism through the ubiquitin-proteasome proteolytic pathway and may play a role in cancer cachexia. *Br J Cancer.* 2005; 93:425-434.
76. Miyajima A, Kosaka T, Asano T, Asano T, Seta K, Kawai T, Hayakawa M. Angiotensin II type 1 antagonist prevents pulmonary metastasis of murine renal cancer by inhibiting tumor angiogenesis. *Cancer Res.* 2002; 62:4176-4179.
77. Szocs K, Lassegue B, Sorescu D, Hilenski L L, Valppu L, Couse T L, Wilcox J N, Quinn M T, Lambeth J D, Griendling K K. Upregulation of Nox-based NAD(P)H oxidases in restenosis after carotid injury. *Arterioscler Thromb Vasc Biol.* 2002; 22:21-27.
78. Jacobson G M, Dourron H M, Liu J, Carretero O A, Reddy D J, Andrzejewski T, Pagano P J. Novel NAD(P)H oxidase inhibitor suppresses angioplasty-induced superoxide and neointimal hyperplasia of rat carotid artery. *Circ Res.* 2003; 92:637-643.
79. Nakamura K, Yamagishi S I, Matsui T, Yoshida T, Takenaka K, Jinnouchi Y, Yoshida Y, Ueda S I, Adachi H, Imaizumi T. Pigment Epithelium-Derived Factor Inhibits Neointimal Hyperplasia after Vascular Injury by Blocking NADPH Oxidase-Mediated Reactive Oxygen Species Generation. *Am J Pathol.* 2007.

The invention claimed is:

1. A method of decreasing angiogenesis in a mammal comprising administering to said mammal an effective amount of an siRNA against p22Phox, said siRNA against p22Phox comprising a sense region and an anti-sense region, wherein said sense region and said anti-sense region form a duplex region, said sense region and said anti-sense region are each 18-30 nucleotides in length and said anti-sense region comprises a nucleotide sequence that is at least 85% complementary to a contiguous sequence of at least 18 nucleotides from position 209 to 279 of the nucleotide sequence of p22phox shown in SEQ ID NO:1, thereby decreasing angiogenesis in said mammal.

2. The method according to claim 1 wherein said method is effective to suppress tumour angiogenesis, stabilize atheromatous plaques or reduce abnormal blood vessel formation.

3. The method of claim 1, wherein said effective amount of said siRNA comprises 5-10 nmol/L of siRNA.

4. The method of claim 1, wherein said administering step takes place intravenously, intradermally, intramuscularly, intrathecally, intranasally, orally, or intraperitoneally.

5. A method of treating tumours comprising administering an effective amount of an siRNA, said siRNA comprising a sense region and an anti-sense region, wherein said sense region and said anti-sense region form a duplex region, said sense region and said anti-sense region are each 18-30 nucleotides in length and said anti-sense region comprises a nucleotide sequence that is at least 80% complementary to a contiguous sequence of at least 18 nucleotides from position 209 to 279 of the nucleotide sequence of p22phox shown in SEQ ID NO:1, thereby treating said tumours.

6. The method of claim 5, wherein said effective amount of said siRNA comprises 5-10 nmol/L of siRNA.

7. The method of claim 5, wherein said administering step takes place intravenously, intradermally, intramuscularly, intrathecally, intranasally, orally, or intraperitoneally.

8. A method of studying an effect of p22phox modulation on a cell comprising contacting the cell with an siRNA, said siRNA comprising a sense region and an anti-sense region, wherein said sense region and said anti-sense region form a duplex region, said sense region and said anti-sense region are each 18-30 nucleotides in length and said anti-sense region comprises a nucleotide sequence that is at least 80% complementary to a contiguous sequence of at least 18 nucleotides from position 209 to 279 of the nucleotide sequence of p22phox shown in SEQ ID NO:1, and detecting one or more physiological and/or chemical changes to the cell, thereby determining the effect of p22phox modulation on said cell.

9. The method according to claim 8, wherein the cell is an endothelial cell.

10. The method according to claim 8, further comprising the step of identifying the effect of p22phox on angiogenesis.

11. The method according to claim 8 additionally comprising the step of contacting a cell with angiotensin II.

12. The method according to claim 8, comprising contacting the cell with a further compound to determine the effect of that further compound on the one or more physiological and/or chemical changes to the cell.

13. The method of claim 8, wherein said contacting step takes place in the presence of 5-10 nmol/L of siRNA.

* * * * *

SEQUENCE LISTING

<160> NUMBER OF SEQ ID NOS: 12

<210> SEQ ID NO 1
<211> LENGTH: 687
<212> TYPE: DNA
<213> ORGANISM: Homo sapiens

<400> SEQUENCE: 1
gcagtgtccc agccgggttc gtgtcgccat ggggcagatc gagtgggcca tgtgggccaa    60
cgagcaggcg ctggcgtccg gcctgatcct catcaccggg ggcatcgtgg ccacagctgg   120
gcgcttcacc cagtggtact ttggtgccta ctccattgtg gcgggcgtgt ttgtgtgcct   180
gctggagtac ccccggggga agaggaagaa gggctccacc atggagcgct ggggacagaa   240
gcacatgacc gccgtggtga agctgttcgg gcccttacc aggaattact atgttcgggc   300
cgtcctgcat ctcctgctct cggtgcccgc cggcttcctg ctggccacca tccttgggac   360
cgcctgcctg ccattgcga gcggcatcta cctactggcg gctgtgcgtg gcgagcagtg   420
gacgcccatc gagcccaagc ccgggagcg ccgcagatc ggaggcacca tcaagcagcc   480
gcccagcaac ccccgccgc ggccccggc cgaggcccgc aagaagccca gcgaggagga   540
ggctgcggcg gcggcggggg accccccggg aggtccccag gtcaaccca tcccggtgac   600 cgacgaggtc gtgtgacctc gccccggacc tgcctccca ccaggtgcac ccacctgcaa   660
taaacgcagc gaaggccggg aaaaaaa                                       687

<210> SEQ ID NO 2
<211> LENGTH: 21
<212> TYPE: DNA
<213> ORGANISM: Homo sapiens

<400> SEQUENCE: 2
aagcacatga ccgccgtggt g                                              21

<210> SEQ ID NO 3
<211> LENGTH: 21
<212> TYPE: DNA
<213> ORGANISM: Homo sapiens

<400> SEQUENCE: 3
aacaccacgg cggtcatgtg c                                              21

<210> SEQ ID NO 4
<211> LENGTH: 21
<212> TYPE: DNA
<213> ORGANISM: Homo sapiens

<400> SEQUENCE: 4
aaccccatcc cggtgaccga c                                              21

<210> SEQ ID NO 5
<211> LENGTH: 21
<212> TYPE: DNA
<213> ORGANISM: Homo sapiens

<400> SEQUENCE: 5
aagtcggtca ccgggatggg g                                              21

<210> SEQ ID NO 6
<211> LENGTH: 21
<212> TYPE: DNA
<213> ORGANISM: Homo sapiens

<400> SEQUENCE: 6
aattactatg ttcgggccgt c                                              21

<210> SEQ ID NO 7
<211> LENGTH: 21
<212> TYPE: DNA
<213> ORGANISM: Homo sapiens

<400> SEQUENCE: 7
aagacggccc gaacatagta a                                              21

<210> SEQ ID NO 8
<211> LENGTH: 19
<212> TYPE: DNA
<213> ORGANISM: Homo sapiens

<400> SEQUENCE: 8
gtccggcctg atcctcatc                                                 19

<210> SEQ ID NO 9
<211> LENGTH: 18
<212> TYPE: DNA
<213> ORGANISM: Homo sapiens

<400> SEQUENCE: 9
gcccgccaca atggagta                                                  18

<210> SEQ ID NO 10
<211> LENGTH: 17
<212> TYPE: DNA
<213> ORGANISM: Homo sapiens

<400> SEQUENCE: 10
cacccagtgg tactttg                                                   17

<210> SEQ ID NO 11
<211> LENGTH: 510
<212> TYPE: DNA
<213> ORGANISM: Rattus norvegicus

<400> SEQUENCE: 11
ccatggggca gatcgagtgg gccatgtggg ccaacgaaca ggcgctggca tctggcctga     60
tcctcatcac aggggggcatc gtggctactg cgggacgctt cacgcagtgg tactttggtg    120
cttactctat tgttgcagga gtgctcatct gtctgctgga gtaccccggg ggaaagagga    180
aaaagggctc caccatggag cggtgtggac agaagtacct gaccgctgtg gtgaagctgt    240
tcgggcccct caccagaaat tactacgtcc gggctgtcct ccacttactg ctgtccgtgc    300
ctgcaggctt cctgctggcc accatcctgg ggaccgtctg cttggccatt gccagtgtga    360
tctacctgct ggcagccatc cggggtgagc agtggactcc cattgagcct aaacccaagg    420
agcggccgca ggttggaggc accatcaagc agccacctac caaccccca ccccggccac    480 cagcggaggt ccgcaagaag ccaagtgagg                                     510

<210> SEQ ID NO 12
<211> LENGTH: 510
<212> TYPE: DNA
<213> ORGANISM: Homo sapiens

<400> SEQUENCE: 12

```
ccatgggca gatcgagtgg gccatgtggg ccaacgagca ggcgctggcg tccggcctga    60
tcctcatcac cggggcatc gtggccacag ctgggcgctt cacccagtgg tactttggtg   120
cctactccat tgtggcgggc gtgtttgtgt gcctgctgga gtaccccgg gggaagagga   180 agaagggctc caccatggag cgctggggac agaagcacat gaccgccgtg gtgaagctgt   240
tcgggcccTT taccaggaat tactatgttc gggccgtcct gcatctcctg ctctcggtgc   300
ccgccggctt cctgctggcc accatccttg ggaccgcctg cctggccatt gcgagcggca   360
tctacctact ggcggctgtg cgtggcgagc agtggacgcc catcgagccc aagccccggg   420
agcggccgca gatcggaggc accatcaagc agccgcccag caacccccccg ccgcggcccc   480 cggccgaggc ccgcaagaag cccagcgagg                                  510
```